(12) United States Patent
Hilfinger et al.

(10) Patent No.: US 8,172,574 B2
(45) Date of Patent: *May 8, 2012

(54) INDICATING TEETH CLEANING TIME

(75) Inventors: Peter Hilfinger, Bad Homburg (DE); Alexander Hilscher, Oberursel (DE); Wolfgang Goecking, Neu Anspach (DE); Peter Trawinski, Weiterstadt (DE)

(73) Assignee: Braun GmbH, Kronberg (DE)

( * ) Notice: Subject to any disclaimer, the term of this patent is extended or adjusted under 35 U.S.C. 154(b) by 191 days.

This patent is subject to a terminal disclaimer.

(21) Appl. No.: 12/700,993

(22) Filed: Feb. 5, 2010

(65) Prior Publication Data

US 2010/0175208 A1    Jul. 15, 2010

Related U.S. Application Data

(63) Continuation-in-part of application No. 10/475,954, filed as application No. PCT/EP02/02417 on Mar. 6, 2002, now Pat. No. 7,682,153.

(30) Foreign Application Priority Data

Apr. 25, 2001 (DE) .................................. 101 20 090

(51) Int. Cl.
A61C 17/22 (2006.01)
A46B 15/00 (2006.01)
(52) U.S. Cl. ....................................... 433/216; 15/167.1
(58) Field of Classification Search .................. 433/216; 15/167.1; 434/263
See application file for complete search history.

(56) References Cited

U.S. PATENT DOCUMENTS

| | | | |
|---|---|---|---|
| 4,450,599 A | 5/1984 | Scheller et al. | |
| 5,438,726 A | 8/1995 | Leite | |
| 5,544,382 A | 8/1996 | Giuliani et al. | |
| 5,561,881 A | 10/1996 | Klinger et al. | |
| 5,687,092 A | 11/1997 | Bretmersky et al. | |
| 5,894,453 A | 4/1999 | Pond | |
| 6,029,303 A | 2/2000 | Dewan | |
| 6,536,068 B1 | 3/2003 | Yang et al. | |
| 6,606,755 B1 | 8/2003 | Robinson et al. | |
| 6,754,928 B1 | 6/2004 | Rosen | |
| 7,682,153 B2 * | 3/2010 | Hilfinger et al. | 433/216 |
| 2003/0017874 A1 | 1/2003 | Jianfei et al. | |

FOREIGN PATENT DOCUMENTS

| | | |
|---|---|---|
| DE | 197 28 964 | 1/1999 |
| EP | 0 210 094 | 6/1986 |
| WO | WO 96/14025 | 5/1996 |
| WO | WO 97/19650 | 6/1997 |

* cited by examiner

Primary Examiner — Ralph Lewis
(74) Attorney, Agent, or Firm — John P. Colbert

(57) ABSTRACT

This disclosure relates to toothbrushes and to methods of operating toothbrushes. In some embodiments, a method of operating a toothbrush includes measuring an actual cleaning time of a first teeth cleaning process, comparing the actual cleaning time of the first teeth cleaning process to a standard cleaning time, and determining a target cleaning time of a second, subsequent teeth cleaning process. In certain embodiments, the target cleaning time of the second teeth cleaning process is the standard cleaning time plus additional time when the actual cleaning time of the first cleaning process is less than the standard cleaning time.

32 Claims, 4 Drawing Sheets

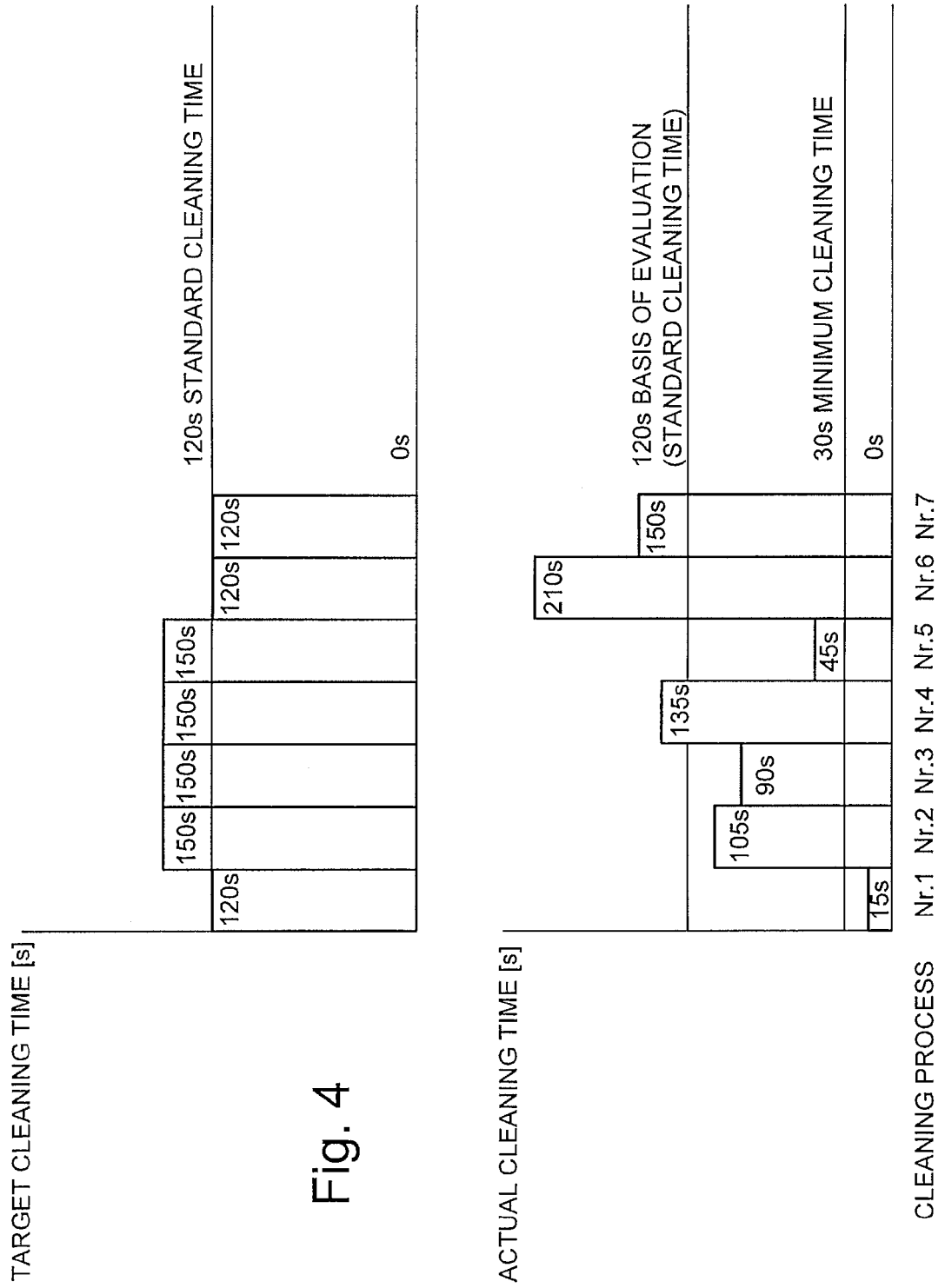

INDICATING TEETH CLEANING TIME

CROSS-REFERENCE TO RELATED APPLICATIONS

This U.S. patent application is a continuation-in-part of, and claims priority under 35 U.S.C. §120 from, U.S. patent application Ser. No. 10/475,954, filed on Mar. 16, 2004, now U.S. Pat. No. 7,682,153, which is a national stage application of International Application No. PCT/EP02/02417, filed on Mar. 6, 2002 which claims priority under 35 U.S.C. §119 to German Application No. 101 20 090.0 filed on Apr. 25, 2001. The disclosures of these prior applications are considered part of the disclosure of this application and are hereby incorporated by reference in their entireties.

TECHNICAL FIELD

The present invention relates to a method for indicating the cleaning time in teeth cleaning.

BACKGROUND

It is known with electric tooth brushes to provide a time switch, which, starting from switching-on of the electric tooth brush, emits a discernible signal after a predetermined time duration for a user. The signals serve to indicate to the user the end of the cleaning time. The user is made aware of the end of the optimal cleaning time through the use of acoustic or optical signals. From WO 96/14025, it is known to not emit an acoustic or optical timer signal, rather instead to switch the drive motor of the tooth brush on and off rapidly so that the drive motor stutters. This can be done while the device is either in the hand or in the mouth of the user.

In addition, it can be provided that the electric tooth brush is switched off after termination of the target cleaning time automatically. This is inexpedient if the timer-signal merely indicates that a partial region of the teeth, such as, for example, a biting quadrant, has been completely cleaned. In WO 97/19650, it therefore proposed to switch again to regular cleaning operation after the stuttered operation, so that the biting quadrant can be cleaned completely according to the desire of the user. As soon as the user changes to another biting quadrant, he can start anew the timing member by means of a button, in order again to be provided the target cleaning time for this new biting quadrant. This method for indicating the target cleaning time does not fulfill the wishes of all tooth brush users, however.

From DE 197 28 964 A1, a tooth brush with a device is known, which signals to the tooth brush user the beginning and end of the optimal tooth cleaning time. On the tooth brush, a knob or slide switch is mounted, with which at the beginning of the teeth cleaning, an acoustic signal can be released, which is repeated automatically after approximately three minutes. In addition, a signal after approximately three months of using the tooth brush can be emitted, whereby the user is informed that the tooth brush should be replaced with a new tooth brush.

U.S. Pat. No. 6,029,303 discloses a manual tooth brush with an electric circuit, which emits a discernible signal regarding the cleaning time. The beginning of the cleaning time can be determined, for example, by means of a movement sensor, which releases a timing member, whereby, at the end of the time, a signal discernible by the user is emitted from the timing member of an electrical circuit. Also, the possibility exists that with the electronic circuit, the entire cleaning time is added up and a further signal from the electronic circuit is then emitted, which falls below the recommended use time of the tooth brush.

SUMMARY

The present invention is based on the object of producing an improved tooth cleaning device as well as an improved method of the above-disclosed type. Along with deviation of the actual cleaning time from the predetermined target cleaning time in an individual case, a mean value for the actual cleaning time can be reached over multiple, separately successive cleaning processes.

The target cleaning time is variably determined, particularly, when predetermined cleaning times are not obtained from the user. An actual cleaning time of the tooth cleaning process is determined by means of a time determination device. By means of an evaluation device, the deviation of the determined actual cleaning time from a predetermined constant or variable standard cleaning time, depending on parameters, is determined. A control device determines the target time for a subsequent tooth cleaning process. This determination depends on the deviation determined by the evaluation device. After termination of the target time, a timer signal is emitted.

The target cleaning time can be adapted personally to the cleaning environment and/or for example, to the daily rhythm of the user. Behind the variable timer-signal, the consideration exists that a combination of short and longer cleaning processes resulting from the variable timer-signal can lead to a good or satisfactory cleaning result, because a cleaning process that was too short is compensated by a lengthened cleaning time in a subsequent cleaning process. The variable standard cleaning time can adopt different values that are user-specific. For example, the variable standard cleaning time may differ between children and adults. It may also be cleaning-tool specific. For example, the variable standard cleaning time may differ depending on the type of implement used, such as a flat brush, inter-dental brush, floss offset or the like.

In a further embodiment of the invention, a cleaning time account is managed, which takes into consideration the deviations of the actual cleaning time from the predetermined standard cleaning time with multiple, previous tooth cleaning processes. Thus, the sum of deviations over multiple tooth cleaning processes is determined. A cleaning time memory can be provided, which stores the sum of deviations between the actual cleaning time and the standard cleaning time determined from multiple tooth cleaning processes. The control device uses the cleaning time memory with the determination of the target cleaning time for a new tooth cleaning process and determines the target cleaning time based on the determined deviations from one or more previous cleaning processes. With multiple deviations, correspondingly marked changes of the target cleaning time take place. In particular, the target cleaning time relative to the standard cleaning time is markedly lengthened when only one shortened tooth cleaning process was performed. Similarly, the target cleaning time relative to the standard cleaning time may be markedly shortened when only one lengthened tooth cleaning was performed.

Preferably, the deviations between actual cleaning time and standard cleaning time only up to a predetermined amount are taken into consideration. In particular, the deviations between the actual cleaning times and the standard cleaning times can be added up only to a known capping limit and can be stored in the cleaning time memory. Upon exceeding the capping limit, the threshold value can be taken into consideration or the target time change can be considered.

It is likewise possible not only to limit the sum of the deviations, but also to provide a capping limit for the individual deviations. If the actual cleaning time deviates too intensely from the predetermined standard cleaning time, only the provided maximum amount of the deviation is considered for the change of the target cleaning time of the next tooth cleaning process. Such a limitation of the considered deviations is based on the conclusion that a known frame and optimal tooth cleanliness cannot be achieved when the fluctuations are too marked. Thus, only deviations within a predetermined range change the target cleaning time.

In particular, it can be provided that the control device determines the target cleaning time always within a predetermined range. This range basically can be formed differently. Thus, in particular, a maximum lengthening of the target cleaning time can be provided.

The range limit for the target cleaning time can be determined differently. According to an advantageous form of the invention, the standard cleaning time can be provided as the minimal target cleaning time. The control device determines the target cleaning time always as greater or the same as the standard cleaning time. When the user positively fills up his cleaning time ledger by too long of a tooth cleaning over the target cleaning time, the timer is not activated before the standard cleaning time by the control device during the next tooth cleaning process.

According to an alternative embodiment of the invention, it can be provided that the target cleaning time can not only be lengthened, but also shortened relative to the standard cleaning time. For the cleaning time account, then, cleaning times over the target cleaning time are also taken into consideration and referenced for the determination of the next target cleaning time. If the user, for example, cleans his teeth in the evening for a particularly long time over the standard cleaning time, a corresponding credit is placed on the cleaning time account and the target cleaning time on the next morning is correspondingly shortened.

The deviations determined with a previous cleaning process or with multiple previous cleaning processes can be taken into consideration in various ways with the determination of the target cleaning time. Thus, it can be provided that the deviations are passed along only in part with the change of the target cleaning time. For example, a cleaning time that lasts 30 seconds over the standard cleaning time can lead to only a 15-second shortening of the next target cleaning time. According to an advantageous embodiment of the invention, the determined deviation or the sum of the determined deviations between actual cleaning times and standard cleaning times is directly abstracted. Thus, a one-to-one determination of the target time to the standard cleaning time is proposed or abstracted. This takes place preferably only within the determined limits, so that the target cleaning time is changed only within the predetermined capping limits.

In a further embodiment of the invention, only tooth cleaning processes that last longer than a minimum time are taken into consideration for the cleaning time account. If the actual cleaning time of a tooth cleaning process lies below the minimum limit, which are determined by different, for example, user- or cleaning-tool-specific factors, no deviation between the actual cleaning time and the standard cleaning time is determined or this is not taken into consideration with the determination of the target cleaning time of a later tooth cleaning process. The minimum time is preferably 30 seconds.

In order to better signal to the user of the tooth cleaning device the adaptation of the time or his deviation from the standard cleaning time, a corresponding warning signal is emitted, which indicates to the user that the last tooth cleaning process was too short and a correspondingly longer target cleaning time is necessary for the current tooth cleaning process. The warning signal is preferably emitted at the beginning of the respective tooth cleaning process.

In a further embodiment of the present invention, it can be provided that upon termination of a tooth cleaning process before reaching the standard cleaning time, a warning signal is emitted, which indicates to the user that he cleaned his teeth for too short of a time. A further warning signal is preferably provided when the tooth cleaning process is interrupted before reaching the respectively variable target cleaning time. Accordingly, the noted warning signals are different from one another, so that it is clear which change or deviation is made or occurred.

In order to achieve a measured determination and evaluation of the actual cleaning times, a coast down timer can be provided. With the determination of the actual cleaning time, temporary interruptions of the tooth cleaning process can be ignored. This can be particularly sensible with a temporary on/off switching of the tooth cleaning device. This may occur, for example, upon changing from one biting quadrant to the next biting quadrant or when tooth paste is removed from the mouth and the tooth brush is turned off temporarily. If the time determination and the corresponding evaluation were run anew each time, few sensible results would be achieved.

In one aspect of the invention, a method of controlling a toothbrush includes measuring an actual cleaning time of a first teeth cleaning process using a time determination device of the toothbrush, comparing the actual cleaning time of the first teeth cleaning process to a standard cleaning time using an evaluation device of the toothbrush, and determining a target cleaning time of a second, subsequent teeth cleaning process using a control device of the toothbrush. The target cleaning time of the second teeth cleaning process is the standard cleaning time plus additional time when the actual cleaning time of the first cleaning process is less than the standard cleaning time.

In another aspect of the invention, a method of controlling a toothbrush includes measuring an actual cleaning time of a first teeth cleaning process using a time determination device of the toothbrush, comparing the actual cleaning time of the first teeth cleaning process to a target cleaning time of the first cleaning process using an evaluation device of the toothbrush, and determining a target cleaning time of a second, subsequent teeth cleaning process using a control device of the toothbrush. The target cleaning time of the second teeth cleaning process is equal to a standard cleaning time plus additional time when the actual cleaning time of the first cleaning process is less than the target cleaning time of the first cleaning process, and the target cleaning time of the second teeth cleaning process is equal to the standard cleaning time when the actual cleaning time of the first cleaning process is greater than or equal to the target cleaning time of the first cleaning process.

In an additional aspect of the invention, a toothbrush includes a tooth cleaning element and a controller that is configured to (1) measure an actual cleaning time of a first teeth cleaning process, (2) compare the actual cleaning time of the first teeth cleaning process to a target cleaning time of the first cleaning process, and (3) determine a target cleaning time of a second, subsequent teeth cleaning process by adding additional time to a standard cleaning time when the actual cleaning time of the first cleaning process is less than the target cleaning time of the first cleaning process.

Embodiments can include one or more of the following embodiments.

In some embodiments, the additional time added to the standard cleaning time is a fixed time such that, when the actual cleaning time of the first cleaning process is less than the standard cleaning time by any of a plurality of different amounts of time, the target cleaning time for the second teeth cleaning process is the standard cleaning time plus the fixed time.

In certain embodiments, the fixed time is at least about 15 seconds (e.g., about 30 seconds).

In some embodiments, the additional time added to the standard cleaning time is equal to a deviation of the actual cleaning time of the first cleaning process from the standard cleaning time when the deviation is less than or equal to a deviation limit.

In certain embodiments, the additional time added to the standard cleaning time is a fixed time for any deviation of the actual cleaning time of the first cleaning process from the standard cleaning time that is greater than the deviation limit.

In some embodiments, the deviation limit is about 90 seconds, and the fixed time is about 90 seconds.

In certain embodiments, the additional time added to the standard cleaning time is equal to the deviation of the actual cleaning time of the first teeth cleaning processes from the standard cleaning time plus the deviation of an actual cleaning time of a third teeth cleaning process from the standard cleaning time, wherein the third teeth cleaning process preceded the first teeth cleaning process.

In some embodiments, the additional time is only added to the standard cleaning time when the actual cleaning time of the first teeth cleaning processes differs from the standard cleaning time by a minimum time differential.

In some embodiments, the target cleaning time of the second teeth cleaning process is the standard cleaning time when the actual cleaning time of the first cleaning process is greater than or equal to the standard cleaning time.

In certain embodiments, the standard cleaning time is about 120 seconds.

In some embodiments, the control device only determines the target cleaning time of the second teeth cleaning process based on the comparison of the actual cleaning time and the target cleaning time of the first teeth cleaning process when the actual cleaning time of the first teeth cleaning process exceeds a minimum cleaning time.

In certain embodiments, the minimum cleaning time is about 30 seconds.

In some embodiments, the method further includes determining a target cleaning time for the first cleaning process based on a comparison of an actual cleaning time and a target cleaning time of a third teeth cleaning process that preceded the first cleaning process.

In certain embodiments, the first and second cleaning processes occur at least about one hour apart from one another.

In some embodiments, the method further includes activating an output device of the toothbrush to alert a user when the target cleaning time of one of the cleaning processes has ended.

In certain embodiments, the output device is an audible alarm.

In some embodiments, a determined deviation of the actual cleaning time of the first cleaning process from the standard cleaning time is stored in memory of the toothbrush.

In certain embodiments, the control device accesses the memory to determine the target cleaning time of the second teeth cleaning process.

In some embodiments, the toothbrush emits a sub-target warning signal if the actual cleaning time of the first teeth cleaning process is determined to be less than the standard cleaning time.

In certain embodiments, the actual cleaning time of the first teeth cleaning process is determined as a time interval between an operator activating and deactivating the toothbrush.

In some embodiments, the actual cleaning time of the first teeth cleaning process continues to be measured upon temporary interruption of operation of the toothbrush if the interruption is less than a minimum interruption time limit.

In certain embodiments, the additional time added to the standard cleaning time is a fixed time such that, when the actual cleaning time of the first cleaning process is less than the target cleaning time of the first cleaning process by any of a plurality of different amounts of time, the target cleaning time for the second teeth cleaning process is the standard cleaning time plus the fixed time.

In some embodiments, the additional time added to the standard cleaning time is equal to a deviation of the actual cleaning time of the first cleaning process from the target cleaning time of the first cleaning process when the deviation is less than or equal to a deviation limit.

In certain embodiments, the additional time added to the standard cleaning time is a fixed time when the deviation is greater than the deviation limit.

In some embodiments, the target cleaning time of the first teeth cleaning process is the standard cleaning time.

In certain embodiments, the control device only determines the target cleaning time of the second teeth cleaning process based on a comparison of the actual cleaning time and the target cleaning time of the first teeth cleaning process when the actual cleaning time of the first teeth cleaning process exceeds a predetermined minimum cleaning time.

In some embodiments, the method further includes determining the target cleaning time of the first cleaning process based on a comparison of an actual cleaning time and a target cleaning time of a third teeth cleaning process that preceded the first cleaning process.

In certain embodiments, the actual cleaning time of the first teeth cleaning process continues to be measured upon temporary interruption of operation of the toothbrush if the interruption is less than a predetermined minimum interruption time limit.

Next, the invention will be described in more detail with reference to a preferred embodiment and associated drawings.

BRIEF DESCRIPTION OF DRAWINGS

FIG. 4 is a diagram illustrating assigned target cleaning times resulting from a system configured to add a fixed time to a standard cleaning time in order to determine the target cleaning time when the target cleaning time of a preceding cleaning process was not achieved.

DETAILED DESCRIPTION

Figure 1:
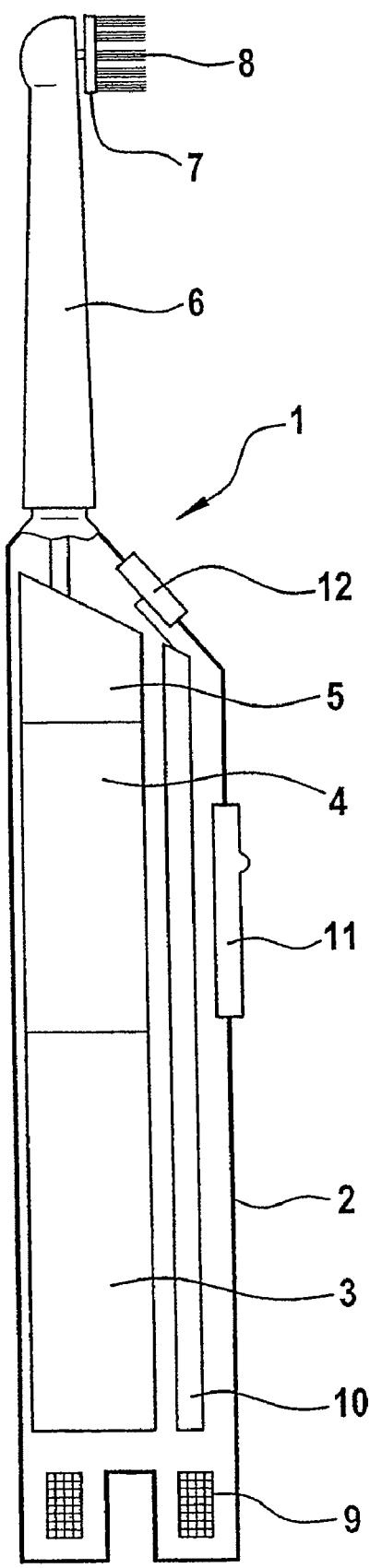
FIG. 1 shows a schematic representation of an electric tooth brush according to the present invention.

In FIG. 1, an electric tooth brush 1 is shown, in which a housing 2, an accumulator 3, a motor 4, and a drive 5 are accommodated. On a free end of the electric tooth brush 1, an attachment brush 6 can be inserted, which has a rotary-supported stiff-bristled support 7 with bristles 8 attached thereto. The bristle-support 7 can be rotary driven in an oscillating manner about a rotational axis that is essentially perpendicular to the longitudinal axis of the attachment brush 6 in a known manner by the motor 4.

In the housing 2 of the tooth brush 1, a coil 9 as well as a control device 10 in the form of a circuit board are accommodated. The coil 9 is arranged on the end of the housing 2 lying opposite the attachment brush 6 and serves for charging the accumulator 3. The control device 10 includes various electronic components, which control the operation of the electric tooth brush 1. Accessible from outside, a switch 11 is arranged in the wall of the housing 2, with which the motor 4 of the tooth brush can be switched on and off. An output unit 12 is arranged in the wall of the housing 2, which is connected with the control unit 10 and serves to emit signals, in particular, a timer signal, for indicating the termination of the target cleaning time. The signals emitted by the output unit 12 can be variously formed, for example, optically or acoustically. Also, other output of the signals can be provided. For example, the motor 11 can be placed into a stuttering operation, such as described in WO 97/19650. Regarding the structure of the timer-signal in this connection, specific reference is made to WO 97/19650.

Figure 2:
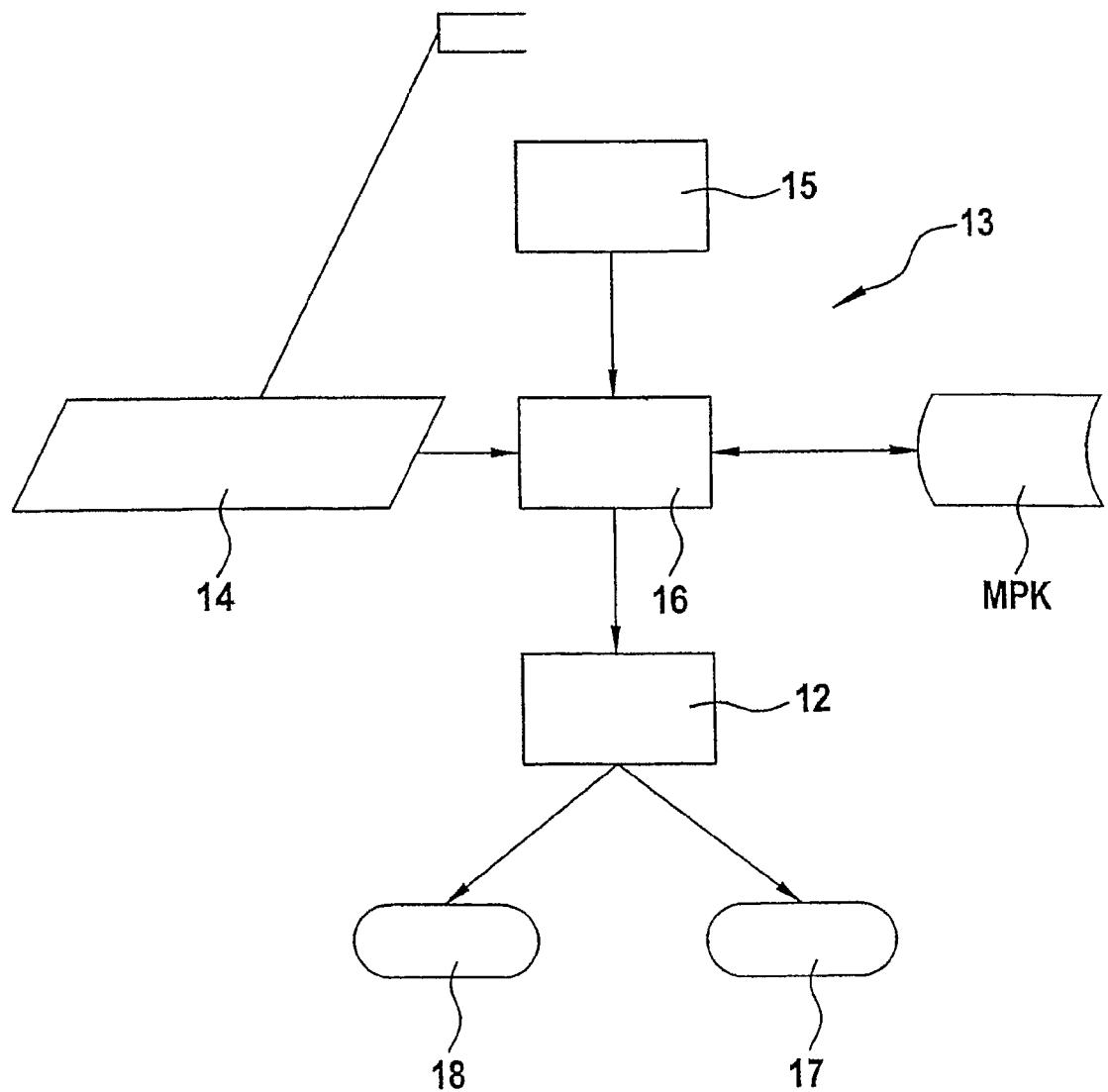
FIG. 2 is a block diagram of a variable timing member of the electric tooth brush according to FIG. 1.

The control device 10 includes, in particular, a timing member or a timer for production of a timer-signal after termination of a target cleaning time. Such a timer is shown in FIG. 2 and is generally designated with reference numeral 13. In a memory 14, first cleaning constants are stored, which dictate the boundary conditions of the target cleaning process. In particular, a standard cleaning time and a minimum cleaning time for an effectual cleaning process can be stored in the memory.

In addition, a time determination device 15 is provided, which can be activated by a switch 11 for switching on the motor 4. Preferably, it includes a coasting down means, so that with temporary interruptions of the motor operation, it continues to run. It determines the time between switching on of the motor 4 and its definite switching off.

A central component of the timer or the timing member for emitting the timer signal is the evaluation device 16, which has access to the memory 14 and which is connected with the time determination device 15 in order to obtain the actual cleaning time. It determines the deviation of the respectively determined actual cleaning times from the standard cleaning times stored in the memory 14. It places the determined deviations on a cleaning time account MPK, and determines with reference to the deviations from previous tooth cleaning process the target cleaning time, after whose termination a timer-signal is emitted. The memory 14 and the cleaning time account MPK can be formed from separate storage components, as shown in the drawing. Alternatively, however, they can also be formed as a common memory.

For outputting the timer signal, the evaluation device 16 is connected with the output unit 12. The output unit 12 can emit a timer-signal 17, which indicates the termination of the variably determined target cleaning time. In addition, the output unit 12 can emit different warning signals 18, which indicate to the user different deviations or changes of the time switch. In particular, a sub-minimum warning signal W1 can be emitted, when a cleaning process is discontinued under the minimum cleaning time. A sub-target warning signal W2 can be emitted, when the user switches off the apparatus before reaching the timer-signal 17. The sub-target warning signal W2 preferably can be distinguished from the first warning signal W1. Finally, in order to note a changed target cleaning time, relative to the standard cleaning time, with the next cleaning process, a non-standard warning signal W3 or advisory signal can be emitted, which is distinguishable from the previous signals and indicates to the user that the timer-time was changed. The named signals can be emitted optically or acoustically. Also, the previously described stuttered-motor can be provided. Other signal output forms are possible.

Figure 3:
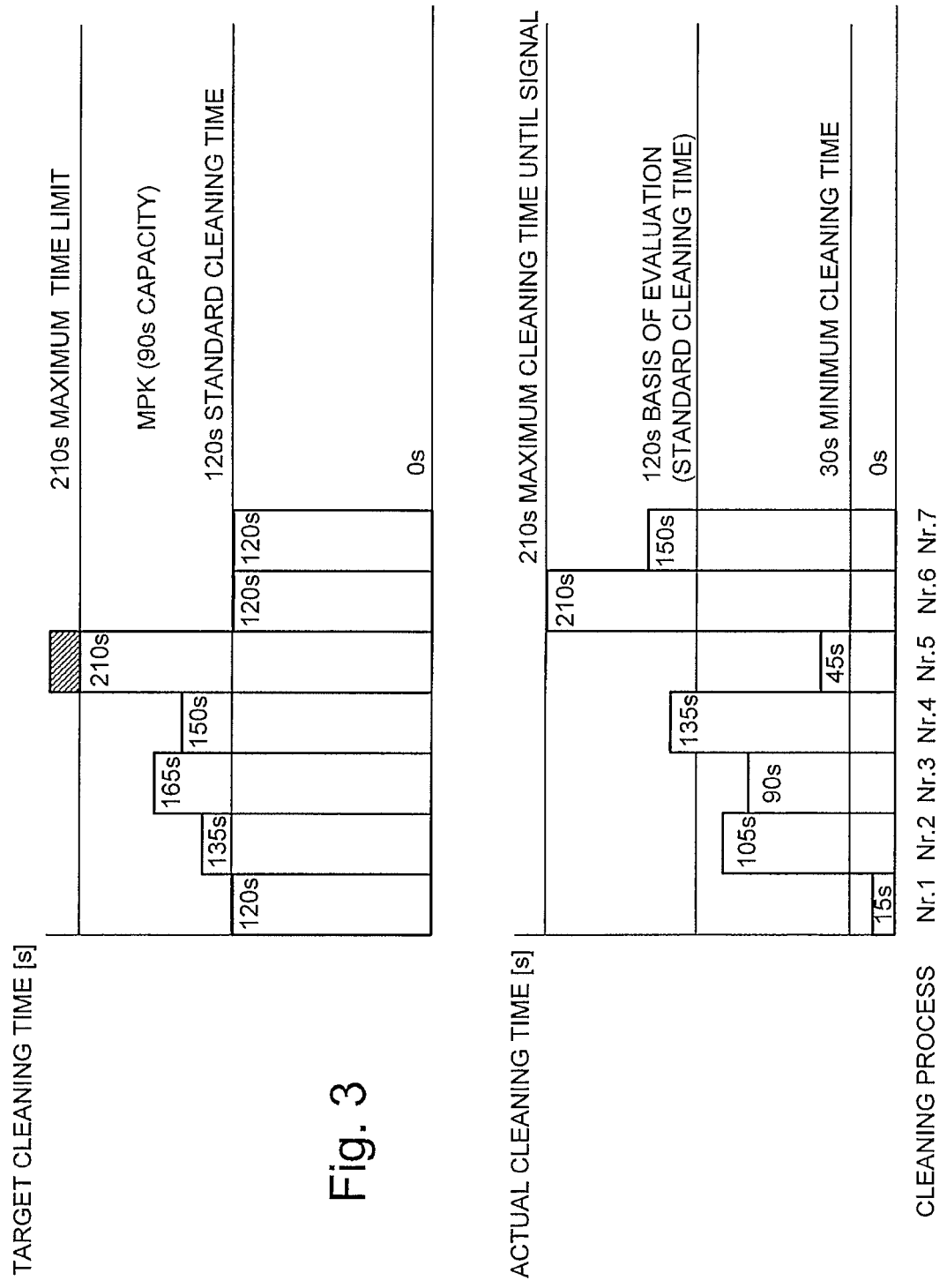
FIG. 3 is a flow diagram of the variable timing member, which makes clear the changes of a cleaning time account over multiple cleaning processes.

Next, the function of the tooth brush 1 and in particular, the timing member 13, will be explained in greater detail with reference to different cleaning processes in connection with FIG. 3.

First, the cleaning time account MPK guided by the evaluation device 16 is empty. For the cleaning time account, a capping limit of 90 seconds is provided, that is, deviations between actual cleaning time and standard cleaning time up to merely a total of 90 seconds can be added up. The cleaning time account has a capacity of 90 seconds. The standard cleaning time stored in the memory 14 amounts to 120 seconds in the shown embodiment. The minimum cleaning time likewise stored in the memory 14 for an effectual cleaning process is determined with 30 seconds.

With a first cleaning process, the user terminates his cleaning process after 15 seconds, without waiting for a signal from the timing member 13. The sub-minimum warning signal W1 indicates that the cleaning process was too short and is not valued for the time balance. Accordingly, the cleaning time account remains empty.

With a second cleaning process, the user terminates his cleaning process after 105 seconds, again without emission of the timer-signal. The warning signal W2 indicates that the recommended standard cleaning time has not been reached. The evaluation device 16 determines the deviation between the actual cleaning time and the stored standard cleaning time. The difference of 105 seconds and 120 seconds, namely, 15 seconds less time, is added to the cleaning time account. The cleaning time account obtains therewith the value of 15 seconds less time.

With a third cleaning process, the timer is reconfigured. The target cleaning time is placed to a value differing from the standard cleaning time. The target cleaning time is set up to the sum of the standard time of 120 seconds and the stored value of 15 seconds, namely, to 135 seconds. In order to make noticeable the now-lengthened cleaning time, this non-standard warning signal W3 sounds directly after the switching on of the tooth brush, in order to indicate to the user that a lengthened target cleaning time is to be obtained. The user, however, terminates his cleaning after 90 seconds without the timer-signal. The sub-target warning signal W2 sounds. The evaluation device 16 determines anew a less time of 30 seconds. This deviation is added to the previously determined deviation, so that the cleaning account is set at a value of 45 seconds.

With a fourth cleaning process, first the timer is adjusted corresponding to the deviations stored in the cleaning time account. On the standard cleaning time of 120 seconds, the sum of the deviations of 45 seconds stored in the cleaning time account is added, so that the target cleaning time is adjusted to 165 seconds. With switching on, the warning signal W3 sounds, which provides the lengthened target cleaning time. The user terminates his cleaning process this time after 135 seconds without the timer-signals. The warning signal W2 sounds anew. This time, however, the value of the cleaning time account is reduced, since the cleaning process lasted longer than the standard cleaning time of 120 seconds. The less-cleaning time is reduced by the difference of 135 seconds to the standard cleaning time of 120 seconds. In the cleaning time account, a less time of now 30 seconds is stored.

With a fifth cleaning process, the target cleaning time corresponding to the less time of 30 seconds is set to 150 seconds, which corresponds to the sum of the standard cleaning time and the stored less cleaning time. Upon switching on, signal W3 sounds anew. The user terminates his cleaning process, however, after 45 seconds without the timer-signal, so that the sub-target warning signal W2 sounds anew. The evaluation device 16 determines a deviation of 75 seconds to the standard cleaning time of 120 seconds. Accordingly, the cleaning time account must be set to a less time of 105 seconds. Since, however, a capping limit of 90 seconds for the cleaning time account is provided, the threshold value of the less time of 90 seconds is stored in the cleaning time account.

According to the maximum less time of 90 seconds, which is stored in the cleaning time account MPK, the target cleaning time and, accordingly, the timer 13 is set to the sum of the standard cleaning time of 120 seconds and the maximum less cleaning time of 90 seconds, that is, to 210 seconds. Upon switching on the tooth brush, the warning signal W3 sounds anew. The user cleans for the set timer time and after 210 seconds, the timer signal 17 is emitted from the output unit 12. Since the target cleaning time would be completely processed, the cleaning time account is reset. The stored less time amounts now to 0 seconds.

In a seventh and last cleaning process according to the illustration, the timer is set to the standard duration of 120 seconds, since in the cleaning time account, no miss-out times are stored. This time, no warning signal sounds upon switching on of the tooth brush. The user cleans until the timer signal, which is emitted after 120 seconds and than for another 30 seconds until to a total cleaning time of 150 seconds. In the shown embodiment, the actual cleaning times over the target cleaning time are not assessed, that is, the cleaning time account is set upon reaching the target cleaning time merely to 0. This was provided in the present case, so that the value of the cleaning time account MPK remains at 0 seconds.

As an alternative to adding/subtracting the time value in the cleaning time account to/from the standard cleaning time in order to determine the target cleaning time of a subsequent cleaning process, other techniques can be used to determine the target cleaning time of the subsequent cleaning process. In certain embodiments, for example, the target cleaning time for the subsequent cleaning process is calculated by adding a fixed time value to the standard cleaning time regardless of the extent to which the actual cleaning time of the preceding cleaning process differed from the standard cleaning process or target cleaning process. The fixed time value that is added to the standard cleaning time is typically at least about 15 seconds (e.g., about 30 seconds, about 60 seconds). Adding such a fixed time value to the standard cleaning time in order to determine the target cleaning time for subsequent cleaning processes can reduce the need for maintaining and updating the cleaning time account. Instead, the control device 10 of the toothbrush can simply assign the standard cleaning time or the increased cleaning time (i.e., standard cleaning time plus fixed time) as the target cleaning time for the subsequent cleaning process depending on whether the target cleaning time of the preceding cycle was achieved or not.

An example of such a method will now be described with reference to FIG. 4. As will be evident, the minimum cleaning time and the standard cleaning time remain unchanged relative to FIG. 3. In addition, the actual cleaning times remain unchanged relative to FIG. 3. Because the target cleaning time will never exceed 150 seconds, as explained below, there is no maximum time limit in this example.

As shown in FIG. 4, the user terminates the first cleaning process after 15 seconds, and thus fails to achieve the minimum cleaning time. As a result, this cleaning process does not register as a full cleaning, and the target cleaning time for the subsequent, second cleaning process is set to the standard cleaning time of 120 seconds.

The user terminates the second cleaning process after 105 seconds, 15 seconds short of the target cleaning time, which in this case is the standard cleaning time of 120 seconds. The evaluation device 16 determines that the actual cleaning time fell short of the target cleaning time. As a result, the target cleaning time for the subsequent, third cleaning process is set to 150 seconds (i.e., the standard cleaning time of 120 seconds plus the fixed time of 30 seconds).

The user terminates the third cleaning process after 90 seconds. The evaluation device 16 determines that the target cleaning time of 150 seconds was not reached and thus sets the target cleaning time for the subsequent, fourth cleaning process to again be 150 seconds (i.e., the standard cleaning time of 120 seconds plus the fixed time of 30 seconds).

The user terminates the fourth cleaning process after 135 seconds. The evaluation device 16 once again determines that the target cleaning time of 150 seconds was not reached and thus sets the target cleaning time for the subsequent, fifth cleaning process to again be 150 seconds (i.e., the standard cleaning time of 120 seconds plus the fixed time of 30 seconds).

The user terminates the fifth cleaning process after 45 seconds. The evaluation device 16 once again determines that the target cleaning time of 150 seconds was not reached and thus sets the target cleaning time for the subsequent, sixth cleaning process to again be 150 seconds (i.e., the standard cleaning time of 120 seconds plus the fixed time of 30 seconds).

The user terminates the sixth cleaning process after 210 seconds, 60 seconds longer than the assigned target cleaning time. The evaluation device 16 determines that the target cleaning time of 150 seconds was reached (and exceeded) and thus sets the target cleaning time for the subsequent, seventh cleaning process to be 120 seconds (i.e., the standard cleaning time).

In the seventh and last cleaning process according to the illustration, the user brushes his/her teeth for 150 seconds, 30 seconds longer than the assigned target cleaning time. The evaluation device 16 again determines that the target cleaning time of 150 seconds was reached and thus sets the target cleaning time for the subsequent cycle to be 120 seconds (i.e., the standard cleaning time).

In certain implementations, time is added to the standard cleaning time (or target cleaning time) to determine the target cleaning time for the subsequent cleaning process only if the actual cleaning time of the preceding cleaning process differed from the standard cleaning time (or target cleaning time of the preceding cleaning process) by at least a minimum time differential. In such embodiments, for example, assuming the minimum time differential is 15 seconds and the actual time of the preceding cleaning cycle differed from the standard cleaning time (or target cleaning time of the preceding cycle)

by only 10 seconds, then time would not be added to the standard cleaning time (or target cleaning time of the preceding cycle) to determine the target cleaning time for the subsequent cleaning process. If, however, the actual time of the preceding cleaning cycle differed from the standard cleaning time (or target cleaning time of the preceding cycle) by 20 seconds, then time would be added to the standard cleaning time (or target cleaning time of the preceding cycle) to determine the target cleaning time for the subsequent cleaning process.

While the fixed time used in the above-described exemplary method was 30 seconds, it should be appreciated that any suitable amount of time can be used as the fixed time.

What is claimed is:

1. A method of controlling a toothbrush, the method comprising:
    measuring an actual cleaning time of a first teeth cleaning process using a time determination device of the toothbrush;
    comparing the actual cleaning time of the first teeth cleaning process to a standard cleaning time using an evaluation device of the toothbrush; and
    determining a target cleaning time of a second, subsequent teeth cleaning process using a control device of the toothbrush, wherein the target cleaning time of the second teeth cleaning process is the standard cleaning time plus additional time when the actual cleaning time of the first cleaning process is less than the standard cleaning time.

2. The method of claim 1, wherein the additional time added to the standard cleaning time is a fixed time such that, when the actual cleaning time of the first cleaning process is less than the standard cleaning time by any of a plurality of different amounts of time, the target cleaning time for the second teeth cleaning process is the standard cleaning time plus the fixed time.

3. The method of claim 2, wherein the fixed time is at least about 15 seconds.

4. The method of claim 3, wherein the fixed time is about 30 seconds.

5. The method of claim 1, wherein the additional time added to the standard cleaning time is equal to a deviation of the actual cleaning time of the first cleaning process from the standard cleaning time when the deviation is less than or equal to a deviation limit.

6. The method of claim 5, wherein the additional time added to the standard cleaning time is a fixed time for any deviation of the actual cleaning time of the first cleaning process from the standard cleaning time that is greater than the deviation limit.

7. The method of claim 6, wherein the deviation limit is about 90 seconds, and the fixed time is about 90 seconds.

8. The method of claim 1, wherein the additional time added to the standard cleaning time is equal to the deviation of the actual cleaning time of the first teeth cleaning processes from the standard cleaning time plus the deviation of an actual cleaning time of a third teeth cleaning process from the standard cleaning time, wherein the third teeth cleaning process preceded the first teeth cleaning process.

9. The method of claim 1, wherein the additional time is only added to the standard cleaning time when the actual cleaning time of the first teeth cleaning processes differs from the standard cleaning time by a minimum time differential.

10. The method of claim 1, wherein the target cleaning time of the second teeth cleaning process is the standard cleaning time when the actual cleaning time of the first cleaning process is greater than or equal to the standard cleaning time.

11. The method of claim 1, wherein the standard cleaning time is about 120 seconds.

12. The method of claim 1, wherein the control device only determines the target cleaning time of the second teeth cleaning process based on the comparison of the actual cleaning time and the target cleaning time of the first teeth cleaning process when the actual cleaning time of the first teeth cleaning process exceeds a minimum cleaning time.

13. The method of claim 12, wherein the minimum cleaning time is about 30 seconds.

14. The method of claim 1, further comprising determining a target cleaning time for the first cleaning process based on a comparison of an actual cleaning time and a target cleaning time of a third teeth cleaning process that preceded the first cleaning process.

15. The method of claim 1, wherein the first and second cleaning processes occur
    at least about one hour apart from one another.

16. The method of claim 1, further comprising activating an output device of the toothbrush to alert a user when the target cleaning time of one of the cleaning processes has ended.

17. The method of claim 16, wherein the output device is an audible alarm.

18. The method of claim 1, wherein a determined deviation of the actual cleaning
    time of the first cleaning process from the standard cleaning time is stored in memory of the toothbrush.

19. The method of claim 18, wherein the control device accesses the memory to determine the target cleaning time of the second teeth cleaning process.

20. The method of claim 1, wherein the toothbrush emits a sub-target warning signal if the actual cleaning time of the first teeth cleaning process is determined to be less than the standard cleaning time.

21. The method of claim 1, wherein the actual cleaning time of the first teeth cleaning process is determined as a time interval between an operator activating and deactivating the toothbrush.

22. The method of claim 1, wherein the actual cleaning time of the first teeth cleaning process continues to be measured upon temporary interruption of operation of the toothbrush if the interruption is less than a minimum interruption time limit.

23. A method of controlling a toothbrush, the method comprising:
    measuring an actual cleaning time of a first teeth cleaning process using a time determination device of the toothbrush;
    comparing the actual cleaning time of the first teeth cleaning process to a target cleaning time of the first cleaning process using an evaluation device of the toothbrush; and
    determining a target cleaning time of a second, subsequent teeth cleaning process using a control device of the toothbrush, wherein
    the target cleaning time of the second teeth cleaning process is equal to a standard cleaning time plus additional time when the actual cleaning time of the first cleaning process is less than the target cleaning time of the first cleaning process; and
    the target cleaning time of the second teeth cleaning process is equal to the standard cleaning time when the actual cleaning time of the first cleaning process is greater than or equal to the target cleaning time of the first cleaning process.

24. The method of claim 23, wherein the additional time added to the standard cleaning time is a fixed time such that, when the actual cleaning time of the first cleaning process is less than the target cleaning time of the first cleaning process by any of a plurality of different amounts of time, the target cleaning time for the second teeth cleaning process is the standard cleaning time plus the fixed time.

25. The method of claim 23, wherein the additional time added to the standard cleaning time is equal to a deviation of the actual cleaning time of the first cleaning process from the target cleaning time of the first cleaning process when the deviation is less than or equal to a deviation limit.

26. The method of claim 25, wherein the additional time added to the standard cleaning time is a fixed time when the deviation is greater than the deviation limit.

27. The method of claim 23, wherein the additional time is only added to the standard cleaning time when the actual cleaning time of the first teeth cleaning processes differs from the target cleaning time of the first teeth cleaning process by a minimum time differential.

28. The method of claim 23, wherein the target cleaning time of the first teeth cleaning process is the standard cleaning time.

29. The method of claim 23, wherein the control device only determines the target
cleaning time of the second teeth cleaning process based on a comparison of the actual cleaning time and the target cleaning time of the first teeth cleaning process when the actual cleaning time of the first teeth cleaning process exceeds a predetermined minimum cleaning time.

30. The method of claim 23, further comprising determining the target cleaning time of the first cleaning process based on a comparison of an actual cleaning time and a target cleaning time of a third teeth cleaning process that preceded the first cleaning process.

31. The method of claim 23, wherein the actual cleaning time of the first teeth cleaning process continues to be measured upon temporary interruption of operation of the toothbrush if the interruption is less than a predetermined minimum interruption time limit.

32. A toothbrush, comprising:
a tooth cleaning element; and
a controller that is configured to
measure an actual cleaning time of a first teeth cleaning process;
compare the actual cleaning time of the first teeth cleaning process to a target cleaning time of the first cleaning process; and
determine a target cleaning time of a second, subsequent teeth cleaning process by adding additional time to a standard cleaning time when the actual cleaning time of the first cleaning process is less than the target cleaning time of the first cleaning process.

* * * * *